(12) United States Patent
Da Costa et al.

(10) Patent No.: US 8,258,189 B2
(45) Date of Patent: Sep. 4, 2012

(54) COMPOUNDS PREPARED BY ADDING AN OXETANE DERIVATIVE TO AN ALCOHOL

(75) Inventors: Georges Da Costa, Saix (FR); Jérôme Guilbot, Castres (FR); Daniel Muller, Saint-Maur (FR); Hervé Rolland, Castres (FR)

(73) Assignee: CECALC, Colombes (FR)

( * ) Notice: Subject to any disclaimer, the term of this patent is extended or adjusted under 35 U.S.C. 154(b) by 72 days.

(21) Appl. No.: 12/682,769

(22) PCT Filed: Sep. 30, 2008

(86) PCT No.: PCT/FR2008/051751
§ 371 (c)(1),
(2), (4) Date: Apr. 12, 2010

(87) PCT Pub. No.: WO2009/050405
PCT Pub. Date: Apr. 23, 2009

(65) Prior Publication Data
US 2010/0216894 A1    Aug. 26, 2010

(30) Foreign Application Priority Data
Oct. 15, 2007   (FR) .................................. 07 58306

(51) Int. Cl.
*A61K 47/00* (2006.01)
*C07C 43/00* (2006.01)
(52) U.S. Cl. ......... 514/772; 568/672; 568/673; 568/675
(58) Field of Classification Search ................. 514/772; 568/673, 672, 675
See application file for complete search history.

(56) References Cited

U.S. PATENT DOCUMENTS

| | | |
|---|---|---|
| 2,854,486 A | 9/1958 | McShane |
| 5,888,482 A | 3/1999 | Amalric et al. |
| 5,958,431 A | 9/1999 | Brancq et al. |
| 6,245,821 B1 | 6/2001 | Bulcourt et al. |
| 6,268,400 B1 | 7/2001 | Amalric et al. |
| 6,353,034 B1 | 3/2002 | Amalric et al. |
| 6,464,993 B1 | 10/2002 | Milius et al. |
| 6,488,946 B1 | 12/2002 | Milius et al. |
| 6,667,396 B2 | 12/2003 | Milius et al. |
| 7,226,580 B2 | 6/2007 | Amalric et al. |
| 7,514,496 B2 | 4/2009 | Amalric et al. |
| 7,651,691 B2 | 1/2010 | Roso et al. |
| 7,652,130 B2 | 1/2010 | Roso et al. |

FOREIGN PATENT DOCUMENTS

| | | |
|---|---|---|
| EP | 0 779 289 | 6/1997 |
| EP | 1 060 740 | 12/2000 |
| FR | 2 668 080 | 4/1992 |
| FR | 2 734 496 | 11/1996 |
| FR | 2 756 195 | 5/1998 |
| FR | 2 762 317 | 10/1998 |
| FR | 2 784 680 | 4/2000 |
| FR | 2 784 904 | 4/2000 |
| FR | 2 790 977 | 9/2000 |
| FR | 2 791 565 | 10/2000 |
| FR | 2 804 432 | 8/2001 |
| FR | 2 807 435 | 10/2001 |
| FR | 2 820 316 | 8/2002 |
| FR | 2 830 445 | 4/2003 |
| FR | 2 830 774 | 4/2003 |
| FR | 2 852 257 | 9/2004 |
| FR | 2 852 258 | 9/2004 |
| FR | 2 858 554 | 2/2005 |
| WO | 94/26694 | 11/1994 |
| WO | 99/36445 | 7/1999 |
| WO | WO 00 27903 | 5/2000 |
| WO | WO 01 14300 | 3/2001 |

OTHER PUBLICATIONS

Zhong et al. et al. 138:106937, 2002.*
Hashimoto et al. CAS: 115: 166678, 1991.*
Fock et al. CAS:107: 178121, 1987.*
PCT Written Opinion for PCT/FR2008/051751, 2008.
International Search Report for PCT/FR2008/051751, 2008.
Evans, R. et al., "Some Ethers of Pentaerythritol and Their Nitrate Esters," J. Am. Chem. Soc., vol. 75, Mar. 1, 1953, pp. 1248-1249.
Fishman, A. et al., "Synthesis and Investigation of Novel Branched PEG-Based Soluble Polymer Supports," J. Org.Chem. vol. 68, No. 25, Dec. 12, 2003, pp. 9843-9846.
Searles, S. et al., "Reactions of Alcohols and Phenols with Trimethylene Oxide," J. Am Chem. Soc., vol. 76, 1954, pp. 56-58.

* cited by examiner

*Primary Examiner* — Rei-tsang Shiao
(74) *Attorney, Agent, or Firm* — RatnerPrestia

(57) ABSTRACT

The invention relates to compositions obtained by the reaction of an alcohol having a variable nature and that can be modified beforehand by the addition of alkylene oxide, and of a substrate characterized by an oxetane pattern and at least one hydroxyl function.

15 Claims, 1 Drawing Sheet

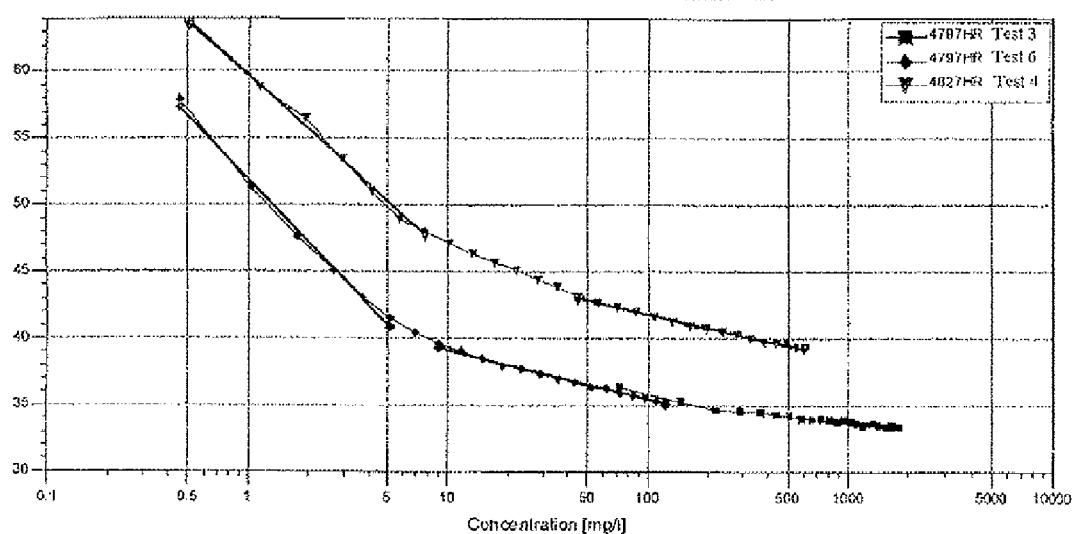
Tensiometric study starting from the R and S derivatives

COMPOUNDS PREPARED BY ADDING AN OXETANE DERIVATIVE TO AN ALCOHOL

This application is a 371 of International PCT Application PCT/FR2008/051751, filed Sep. 30, 2008, the entire contents of which are incorporated herein by reference.

FIELD OF THE INVENTION

A subject matter of the invention is novel compounds obtained from a reaction of an alcohol of variable nature, which can be modified beforehand by addition of alkylene oxide, and a substrate which is characterized by an oxetane unit and by at least one hydroxyl functional group, the process for the preparation of these compositions and their use as non-ionic surface-active agents.

BACKGROUND

A surface-active agent is a chemical substance or composition which, even used in a small amount, significantly reduces the surface tension, in particular that of water, or the surface tension between two immiscible liquids, so as to facilitate the mixing of these two liquids.

Furthermore, the amphiphilic structure of surface-active agents confers on them a particular affinity for interfaces of air/water and water/oil type and thus thereby gives them the ability to lower the free energy of these surfaces. This phenomenon is the basis for the stabilization of dispersed systems.

In the publication "*Reactions of alcohols and phenols with trimethylene oxide*", S. Searles and C. F. Butler, JACS, 1954, Vol. 76, pp. 56-58, the opening of unsubstituted 1,3-propylene oxide or oxetane by various alcohols in the presence of an acidic or basic catalyst:

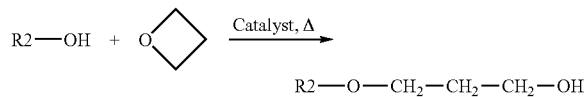

is described.

Nevertheless, the list of the alcohols studied is restricted to alcohols not comprising an alkyl chain capable of conferring an amphiphilic or surface-active nature on the structure of the final adducts (methanol, ethanol, propanol, butanol, isopropanol, benzyl alcohol, phenol alcohols) and the use of non-hydroxylated oxetane does not make it possible to increase the functionality of the final adducts and thus to result in structures having a suitably pronounced polarity.

Patent application WO 01/14300 describes a process for the manufacture of ether alcohols from a hydroxylated oxetane and from a polyol derived from monosubstituted or disubstituted 1,3-propanediol; the molar stochiometries employed systematically involve a deficiency in hydroxylated oxetane not making possible the reduction in the hydroxyl functional groups.

Patent application EP 1 060 740 describes the preparation of polyol ethers or polyol hydroxyethers by reaction of trimethylolpropane, trimethylolbutane, pentaerythritol or dipentaerythritol with saturated or unsaturated fatty alcohols or saturated or unsaturated fatty epoxides, said preparation not involving a derivative of oxetane type among the reactants.

In the context of their research studies on the development of novel surface-active agents, the inventors have developed novel structures resulting from the condensation of oxetane synthons with fatty alcohol derivatives.

SUMMARY OF THE INVENTION

The invention relates to compounds and compositions obtained by the reaction of an alcohol having a variable nature and that can be modified beforehand by the addition of alkylene oxide, and of a substrate characterized by an oxetane pattern and at least one hydroxyl function. The invention further relates to a process for preparing the compound, the use of the compounds as surface active agents, cosmetic, pharmaceutical, detergent, or degreasing formulations that include the surface active agent.

BRIEF DESCRIPTION OF THE FIGURES

FIG. 1 provides a tensiometric study starting from the R and S derivatives.

DETAILED DESCRIPTION OF THE INVENTION

This is why, according to a first aspect, a subject matter of the invention is a compound of formula (I):

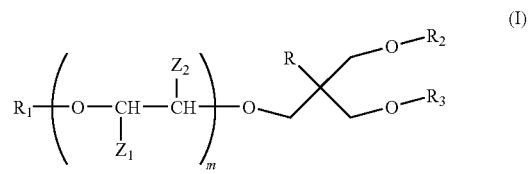

in which:

$R_1$ represents a linear or branched and saturated or unsaturated aliphatic radical comprising from 3 to 24 carbon atoms and preferably from 7 to 24 carbon atoms, optionally substituted by one or more hydroxyl groups, R represents a linear or branched alkyl radical comprising from 1 to 8 carbon atoms, optionally substituted by a hydroxyl radical, m represents a number greater than or equal to 0 and less than or equal to 150, $Z_1$ and $Z_2$, which are identical or different, are chosen from H, $CH_3$ or $CH_2$—$CH_3$, $R_2$ and $R_3$, which are identical or different, represent either a hydrogen atom or a monovalent radical of formula:

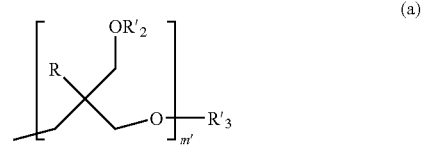

in which:

m' represents a number less than or equal to 10,

R'$_2$ represents either a hydrogen atom or a

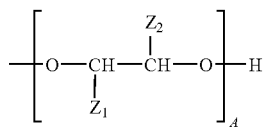

(b)

in which:

R$_1$ and Z$_2$ are as defined above,

A represents an integer greater than or equal to 0 and less than or equal to 50, R'$_3$, which is identical to R'$_2$ or different from R'$_2$, represents either a hydrogen atom or a monovalent radical of formula:

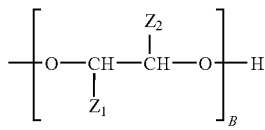

(c)

in which:

Z$_1$ and Z$_2$ are as defined above,

B represents an integer greater than or equal to 0 and less than or equal to 50, with A+B greater than or equal to 0 and less than or equal to 50 and m+A+B≠0.

According to one form of the invention, the formula (a) is:

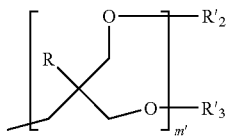

Preferably, A+B is less than or equal to 30 and more particularly less than or equal to 10. Advantageously, m represents a number less than or equal to 50. Preferably, m+A+B is less than or equal to 50 and more particularly less than or equal to 30.

According to a specific form of the invention, m, A and B each represent a number less than or equal to 10.

A composition comprising a mixture of compounds of formula (I) is also a subject matter of the present invention.

According to one aspect of the invention, in the formula (I) as defined above, R'$_2$ and R'$_3$ are hydrogen atoms; in this specific case, the formula (I) is then denoted (I$_1$):

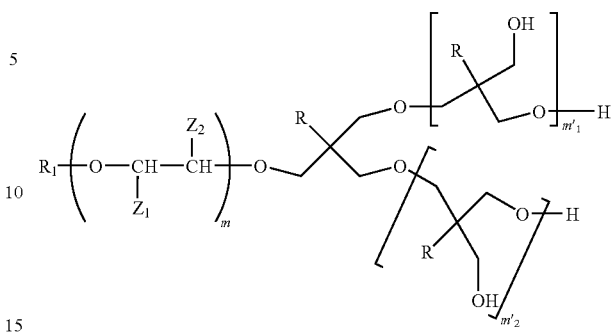

(I$_1$)

in which m'$_1$ and m'$_2$ represent numbers greater than or equal to 0 and less than or equal to 10.

According to one aspect of the present invention, in the formula (I) as defined above, R$_2$ represents a hydrogen atom and R$_3$ represents a radical of formula (a'):

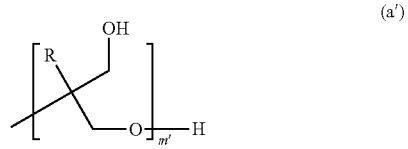

(a')

corresponding to the formula (a) in which R'$_2$ and R'$_3$ each represent a hydrogen atom; this formula will be denoted (Io).

According to another aspect of the invention, in the formula (I) as defined above, R$_2$ and R$_3$ represent a radical of formula (a'):

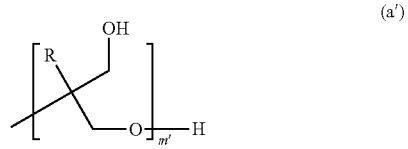

(a')

corresponding to the formula (a) in which R'$_2$ and R'$_3$ each represent a hydrogen atom; this formula will be denoted (I'o).

According to another aspect of the present invention, in the formula (I) as defined above, R$_2$ or R$_3$ is not hydrogen.

In the formula (I), A can without distinction be equal to B or different from B.

The term "linear or branched alkyl radical comprising from one to eight carbon atoms, optionally substituted by a hydroxyl radical," denotes, for R in the formulae defined above: the methyl, ethyl, propyl, isopropyl, butyl, isobutyl, tert-butyl, pentyl, neopentyl, hexyl, heptyl, octyl or methylol radicals.

The term "alcohol of variable nature" is understood to mean saturated or unsaturated linear hydrocarbon fatty alcohols exhibiting a number of carbon atoms ranging from C-8 to C-24 (R$_1$). These alcohols can also be branched alcohols exhibiting a number of carbon atoms ranging from C-8 to C-36, such as, for example, isostearyl alcohol, alcohols resulting from the "oxo" synthesis process, Guerbet alcohols, or dimer diols or alcohols originating from the hydrogenation of the dimer acid having 36 carbon atoms, sold in particular by Cognis or Sidobre-Sinnova under the name Speziol C36/2, or can be functionalized by one or more hydroxyl units, such as hydroxystearyl alcohol, for example.

The term "oxetane derivative exhibiting at least one hydroxyl functional group" is understood to mean the following substrates: trimethylolethane-oxetane (R=Me), trimethylolpropane-oxetane (R=Et), trimethylolbutane-oxetane (R=Pr), trimethylolpentane-oxetane (R=Bu), trimethylolhexane-oxetane (R=—CH$_5$H$_{11}$), trimethylolheptane-oxetane (R=C$_6$H$_{13}$), trimethyloloctane-oxetane (R=C$_7$H$_{15}$), trimethylol-nonane-oxetane (R=—C$_8$H$_{17}$) or pentaerythritol-oxetane (R=—CH$_2$OH).

Another subject matter of the invention is a process for the preparation of a compound of formula (I$_1$) as defined above, comprising the stage:

(a) reaction of at least one alcohol of formula:

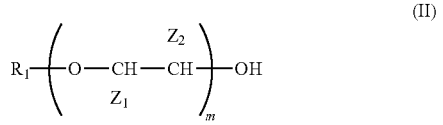

in which R$_1$, Z$_1$ and Z$_2$ are as defined in the formula (I); and at least one substrate, comprising an oxetane unit and at least one hydroxyl functional group, of formula:

in which R is as defined in the formula (I).

During this stage (a), the opening of the oxetane unit is systematically accompanied by the formation of a new hydroxyl functional group which thus makes it possible to progressively increase the functionality of the final surface-active agents with respect to the starting alcohol. By way of example, an adduct with three open oxetane units will exhibit 4 hydroxyl functional groups, as represented by the structural example below:

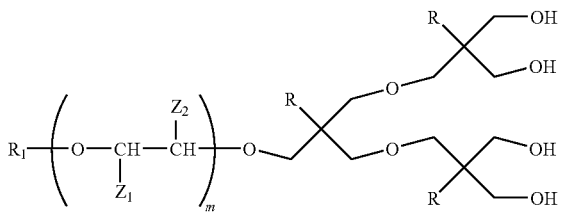

and more generally n oxetane units will result in n+1 hydroxyl functional groups. This configuration can then result, according to the molar stochiometry of starting oxetane derivative, in distributions having pseudodendritic structures.

The presence of these hydroxyl functional groups thus confers, on the products, a more or less pronounced hydrophilicity related to the number of equivalents of oxetane derivative added and to the lipophilic nature of the starting alcohols used.

According to one aspect of the process as defined above, stage (a) of reaction of an alcohol of variable nature of formula (II) and a substrate of formula (III) comprising an oxetane unit and at least one hydroxyl functional group is accompanied by a catalyst 1, such as a Brönsted acid and/or a Lewis acid. More particularly, the catalyst 1 is chosen from sulfuric, sulfonic, hydrochloric, nitric, phosphoric, methanesulfonic, p-toluenesulfonic or trifluoromethanesulfonic acid, boron trifluoride, aluminum trichloride or tin tetrachloride.

According to another aspect of the process as defined above, it additionally comprises the stage:

(b) alkoxylation reaction of the compound of formula (I$_1$) as defined above, accompanied by a catalyst 2 and by an alkylene oxide or a mixture of alkylene oxides or by an alkylene carbonate or a mixture of alkylene carbonates. The catalyst 2 is a basic catalyst, such as potassium hydroxide, sodium hydroxide, sodium methoxide, potassium methoxide, sodium tert-butoxide or potassium tert-butoxide, or a Lewis base, such as triphenylphosphine, or a coordination catalyst, such as, for example, organometallic complexes based on cobalt and/or zinc, or a Lewis acid, such as boron trifluoride, aluminum trichloride or tin tetrachloride. The alkylene oxide or the mixture of alkylene oxides used in such alkoxylation reactions are ethylene oxide, propylene oxide or butylene oxide. In view of the hydrophobic nature of the propoxy or butoxy sequences, the use of ethylene oxide will be favored.

During this new optional stage (b), the alkoxylation reactions adjust the Hydrophilic/Lipophilic Balance (HLB) of the structures of formula (I) described above. This amphiphilicity has resulted in these novel molecules being put to use as surface-active agents having surfactant, wetting, foaming and emulsifying properties which are superior to the properties of known agents.

Another subject matter of the invention is thus the use of a compound of formula (I) as defined above as nonionic surface-active agent and more particularly as foaming agent, emulsifying agent, wetting agent, dispersing agent or detergent agent. A composition comprising a mixture of at least one compound of formula (I), (I$_1$), (I$_2$) and (II) is also a subject matter of the present invention.

Another subject matter of the invention is a detergent or degreasing formulation, characterized in that it comprises, as surface-active agent, at least one compound of formula (I) as defined above and/or a composition comprising a mixture of at least one compound of formula (I), (I$_1$), (I$_2$) and (II).

Finally a subject matter of the invention is a cosmetic or pharmaceutical formulation, characterized in that it comprises, as surface-active agent, a compound of formula (I) as defined above and/or a composition comprising a mixture of at least one compound of formula (I), (I$_1$), (I$_2$) and (II).

The term "cosmetic or pharmaceutical formulation" is understood to mean the formulations which are intended for topical use or else in any type of support intended to be brought into contact with the skin (paper, wipe, textile, transdermal device, and the like). These formulations can be applied to the skin, to the hair, to the scalp and to the mucous membranes, and are provided in particular in the form of an aqueous or oily solution, of an emulsion or microemulsion of the water-in-oil (W/O) or oil-in-water (O/W) type, of the multiple emulsion of water-in-oil-in-water (W/O/W) or oil-in-water-in-oil (O/W/O) type, of a gel, of a soap or syndet, of a balm, of a hydrodispersion, of an ointment, of a cream, of a foam or of an aerosol or any anhydrous form, such as a powder. These formulations can be used as cleansing or makeup-removing milks, as cleansing or makeup-removing lotions, as foaming gels for the face or for the body, as shampoos or conditioners, as foaming baths, as body care creams or as creams or lotions for treating the scalp.

Generally, these formulations comprise, in addition to the compounds of formula (I) and/or the compositions comprising a mixture of at least one compound of formula (I), ($I_1$), ($I_2$) and (II), excipients and/or active principles employed generally in the field of formulations for topical, use, in particular cosmetic, dermocosmetic, pharmaceutical or dermopharmaceutical formulations, such as thickeners, gelling agents, stabilizing agents, film-forming compounds, solvents and cosolvents, hydrotropic, agents, plasticizing agents, fatty substances, oils, emulsifying agents and coemulsifying agents, opacifying agents, pearlescent agents, superfatting agents, sequestering agents, chelating agents, antioxidants, fragrances, preservatives, conditioning agents, whitening agents intended for bleaching hairs and the skin, active principles intended to contribute a treating action with regard to the skin or hair, sunscreens, pigments or inorganic fillers, particles which provide a visual effect or which are intended for the encapsulation of active principles, exfoliating particles, texturing agents, optical brighteners or insect repellents.

Examples of thickening and/or emulsifying polymers used in the cosmetic or pharmaceutical formulations of the present invention include homopolymers or copolymers of acrylic acid or of acrylic acid derivatives, homopolymers or copolymers of methacrylic acid or of methacrylic acid derivatives, homopolymers or copolymers of acrylamide, homopolymers or copolymers of acrylamide derivatives, homopolymers or copolymers of acrylamidomethylpropanesulfonic acid, homopolymers or copolymers of vinyl monomers, homopolymers or copolymers of trimethylammonioethyl acrylate chloride, hydrocollaids of plant or biosynthetic origin, for example xanthan gum, karaya gum, carrageenates or alginates, silicates, cellulose and its derivatives, starch and its hydrophilic derivatives, or polyurethanes. Examples of polymers of polyelectrolyte type, which can be deployed in the production of a gel aqueous phase capable of being used in the preparation of W/O, O/W, W/O/W or O/W/O emulsions or an aqueous gel comprising the Potentille extracts which are subject matters of the present invention, include copolymers of acrylic acid and of 2-methyl-2-[(1-oxo-2-propenyl)amino]-1-propanesulfonic acid (AMPS), copolymers of acrylamide and of 2-methyl-2-[(1-oxo-2-propenyl)amino]-1-propanesulfonic acid, copolymers of 2-methyl-2[(1-oxo-2-propenyl)amino]-1-propanesulfonic acid and of 2-hydroxyethyl acrylate, the homopolymer of 2-methyl-2-[(1-oxo-2-propenyl)amino]-1-propanesulfonic acid, the homopolymer of acrylic acid, copolymers of acryloylethyltrimethylammonium chloride and of acrylamide, copolymers of AMPS and of vinylpyrrolidone, copolymers of acrylic acid and of alkyl acrylates, the carbon chain of which comprises between ten and thirty carbon atoms, and copolymers of AMPS and of alkyl acrylates, the carbon chain of which comprises between ten and thirty carbon atoms. Such polymers are sold respectively under the names Simulgel™ EG, Sepigel™ 305, Simulgel™ NS, Simulgel™ 800, Simulgel™ A, Simulgel™ EPG, Simulgel™ INS, Simulgel™ FL, Sepigel™ 501, Sepigel™ 502, Sepiplus™ 250, Sepiplus™ 265, Sepiplus™ 400, Sepinov™ EMT 10, Carbopol™, Ultrez™ 10, Aculyn™, Pemulen™ TR1, Pemulen™ TR2, Luvigel™ EM, Salcare™ SC91, Salcare™ SC92, Salcare™ SC95, Salcare™ SC96, Flocare™ ET100, Flocare™ ET58, Hispagel™, November™ EC1, Aristoflex™ AVC, Aristoflex™ HBM, Rapithix™ A60, Rapithix™ A100, Cosmedia SP and Stabileze™ 06.

Mention may be made, as examples of thickening and/or gelling surfactants optionally present in the cosmetic or pharmaceutical formulation which is a subject matter of the present invention, of:

optionally alkoxylated fatty esters of alkyl polyglycosides and very particularly ethoxylated esters of methylpolyglucoside, such as PEG-120 methyl glucose trioleate and PEG-120 methyl glucose dioleate, sold respectively under the names Glucamate™ LT and Glumate™ DOE 120;

alkoxylated fatty esters, such as PEG-150 pentaerythrityl tetrastearate, sold under the name Crothix™ DS53, or PEG-55 propylene glycol oleate, sold under the name Antil™ 141;

carbamates of polyalkylene glycols comprising fatty chains, such as PPG 14 laureth isophoryl dicarbamate, sold under the name Elfacos™ T211, or PPG 14 palmeth 60 hexyl dicarbamate, sold under the name Elfacos™ GT2125.

Mention may be made, as examples of emulsifiers optionally present in the cosmetic or pharmaceutical formulation which is a subject matter, of:

fatty acids, ethoxylated fatty acids, fatty acid esters of sorbitol, ethoxylated fatty acid esters, polysorbates, polyglycerol esters, ethoxylated fatty alcohols, sucrose esters, alkylpolyglycosides, sulfated and phosphated fatty alcohols or the mixtures of alkylpolyglycosides and of fatty alcohols described in French patent applications 2 668 080, 2 734 496, 2 756 195, 2 762 317, 2 784 680, 2 784 904, 2 791 565, 2 790 977, 2 807 435, 2 804 432, 2 830 774 and 2 830 445, combinations of emulsifying surfactants chosen from alkylpolyglycosides, combinations of alkylpolyglycosides and of fatty alcohols, or polyglycerol or polyglycol or polyol esters, such as the polyglycol or polyglycerol polyhydroxystearates employed in French patent applications 2 852 257, 2 858 554, 2 820 316 and 2 852 258.

Mention may be made, as examples of opacifying and/or pearlescent agents optionally present in the cosmetic or pharmaceutical formulation which is a subject matter of the present invention, of sodium or magnesium palmitates, sodium or magnesium stearates, sodium or magnesium hydroxystearates, ethylene glycol monostearates or distearates, polyethylene glycol monostearates or distearates, fatty alcohols or styrene homopolymers and copolymers, such as the styrene/acrylate copolymer sold under the name Montopol™ OP1 by SEPPIC.

Mention may be made, as examples of oils optionally present in the cosmetic or pharmaceutical formulation which is a subject matter of the present invention, of:

mineral oils, such as liquid paraffin, liquid petrolatum, isoparaffins and white mineral oils;

oils of animal origin, such as squalene or squalane;

vegetable oils, such as phytosqualane, sweet almond oil, coconut oil, castor oil, jojoba oil, olive oil, rapeseed oil, peanut oil, sunflower oil, wheat germ oil, corn germ oil, soybean oil, cottonseed oil, alfalfa oil, poppy oil, pumpkinseed oil, evening primrose oil, millet oil, barley oil, rye oil, safflower oil, candlenut oil, passionflower oil, hazelnut oil, palm oil, shea butter, apricot kernel oil, calophylium oil, sisymbrium oil, avocado oil, calendula oil or oils resulting from flowers or vegetables;

ethoxylated vegetable oils;

synthetic oils, such as fatty acid esters, for example butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, such as glycerol triheptanoate, alkyl benzoates, hydrogenated oils, poly(α-olefin)s, polyolefins, such as polyisobutene, synthetic isoalkanes, such as isohexadecane or isododecane, or perfluorinated oils, and silicone oils, such as polydimethylsiloxanes, polymethylphenylsiloxanes, silicones modified by amines, silicones modified by fatty acids, silicones modified by alcohols, silicones modified by fatty acids and alcohols, silicones modified by polyether groups, epoxy-modified silicones, silicones modified by fluorinated groups, cyclic silicones and silicones modified by alkyl groups.

Mention may be made, as other fatty substance optionally present in the cosmetic or pharmaceutical formulation which is a subject matter of the present invention, of fatty alcohols or fatty acids; waxes, such as beeswax, carnauba wax, candelilla wax, ouricury wax, Japon wax, cork fiber wax, sugarcane wax, paraffin waxes, lignite waxes, microcrystalline waxes, lanoline wax; ozokerite; polyethylene wax, silicone waxes; vegetable waxes, fatty alcohols and fatty acids which are solid at ambient temperature; or glycerides which are solid at ambient temperature.

Mention may be made, as foaming and/or detergent surfactants optionally present in the cosmetic or pharmaceutical formulation which is a subject matter of the present invention, of: topically acceptable anionic, cationic, amphoteric or nonionic surfactants used generally in this field of activity.

Mention will in particular be made, among the anionic surfactants which can be used in the present invention, of the alkali metal salts, alkaline earth metal salts, ammonia salts, amine salts or aminoalcohol salts of the following compounds: alkyl ether sulfates, alkyl sulfates, alkylamido ether sulfates, alkylaryl polyether sulfates, monoglyceride sulfates, α-olefinsulfonates, paraffinsulfonates, alkyl phosphates, alkyl ether phosphates, alkylsulfonates, alkylamidesulfonates, alkylarylsulfonates, alkylcarboxylates, alkyl sulfosuccinates, alkyl ether sulfosuccinates, alkylamide sulfosuccinates, alkyl sulfoacetates, alkylsarcosinates, acylisethionates, N-acyltaurates or acyl lactylates. Mention will also be made, among the anionic surfactants, of lipoamino acids, lipoproteins, liopeptides, lipoprotein derivatives, protein derivatives, salts of fatty acids or salts of acids of optionally hydrogenated coconut oil.

Mention will particularly be made, among the amphoteric surfactants which can be used in the present invention, of alkyl betaines, alkyl amido betaines, sultaines, alkyl amidoalkyl sulfobetaines, imidazoline derivatives, phosphobetaines, amphopolyacetates and amphopropionates.

Mention will particularly be made, among the cationic surfactants which can be used in the present invention, of quaternary ammonium derivatives.

Mention will particularly be made, among the nonionic surfactants which can be used in the present invention, of alkylpolyglycosides, castor oil derivatives, polysorbates, coconut amides, N-alkylamines or amine oxides.

Mention may be made, as examples of active principle which can be used in the cosmetic or pharmaceutical formulation which is a subject matter of the present invention, of the compounds having a lightening or depigmenting action, such as, for example, arbutin, kojic acid, hydroquinone, ellagic acid, vitamin C and its derivatives, magnesium ascorbyl phosphate, Sepiwhite™ MSH, Sepicalm™ VG, polyphenol extracts, grape extracts, pine extracts, wine extracts, olive extracts, marc extracts, apple juice extracts, N-acylated proteins, N-acylated peptides, N-acylated aminoacids, such as, for example, N-lauroylproline, N-linoleyllysine, N-linoleylleucine, N-octanoylglycine, N-undecylenoylphenylalanine or N-palmitoylproline, partial hydrolysates of N-acylated proteins, aminoacids, peptides, total hydrolysates of proteins, partial hydrolysates of proteins, polyols (for example glycerol or butylenes glycol), urea, pyrrolidonecarboxylic acid or the derivatives of this acid, glycyrrhetinic acid, α-bisabolol, sugars or sugar derivatives, polysaccharides or their derivatives, hydroxy acids, for example lactic acid, vitamins, vitamin derivatives, such as retinol, retinal derivatives, vitamin E and its derivatives, minerals, enzymes, coenzymes, such as coenzyme Q10 and its derivatives, hormones or "hormone-like" substances, soybean extracts, for example Raffermine™, wheat extracts, for example Tensine™ or Gliadine™, plant extracts, such as extracts rich in tannins, extracts rich in isoflavones or extracts rich in terpenes, extracts of fresh water or marine algae, essential waxes, bacterial extracts, minerals, lipids in general, lipids such as ceramides or phospholipids, active principles having a tanning action, such as dihydroxyacetone and/or erythrulose, active principles having a slimming action, such as caffeine or its derivatives, active principles having an antimicrobial activity or a purifying action with regard to greasy skin, such as Deepaline™ PVB or Lipacide™ UG, active principles having an energizing or stimulating property, such as, for example, Sepitonic™ M3 or Physiogenyl™, panthenol and its derivatives, such as Sepicap™ MP, antiaging active principles, such as Sepilift™ DPHP, Deepaline™ PVB, Sepivinol™ or Sepivital™, moisturizing active principles, such as Sepicalm™ S, Sepicalm™ VG and Sepilift™ DPHP, Aquaxyl™ or Preteol™ SAV 50, antiaging active principles, active principles exhibiting an immediate smoothing or tightening action on the skin, such as Sesaflash, "anti-photoaging" active principles, active principles which protect the integrity of the dermoepidermal junction, active principles which increase the synthesis of the components of the extracellular matrix, active principles having a slimming, firming or draining activity, such as caffeine, theophylline, cyclic adenosine monophosphate (cAMP), green tea, sage, *ginkgo biloba*, ivy, horse chestnut, bamboo, ruscus, butcher's broom, *Centella asiatica*, heather, meadowsweet, fucus, rosemary, willow or extracts of parsnip, active principles which create a feeling of "heating" on the skin, such as activators of cutaneous microcirculation (example of nicotinates), or products which create a feeling of "coolness" on the skin (example of menthol and derivatives), active principles exhibiting an action with regard to stem cells, active principles exhibiting an action on the epidermis, dermis, hypodermis and skin appendages (hairs, sebaceous glands, pores, and the like), or active principles exhibiting an action with regard to the skin flora.

Mention may be made, as sunscreen which can be incorporated in the cosmetic or pharmaceutical formulation which is a subject matter of the invention, of all those appearing in the Cosmetics Directive 76/768/EEC, amended, Annex VII.

All the compounds of formulae (I), ($I_1$), (II) and (III) are to be considered in any possible stereoisomeric form.

The following experimental part illustrates the invention without, however, limiting it.

Example 1

Preparation of Amphiliphilic Structures

Stage a): Opening of the Oxetane Derivative by the Alcohol:

The opening of the oxetane derivative by the alcohol is carried out in the presence of an acid catalyst at a temperature of between 80° C. and 160° C., preferably at 120° C. The amount of catalyst introduced is between 0.1 and 1.0%, with respect to the entire starting medium. The molar stochiometry of oxetane derivative, with respect to the alcohol used, is between 0.5 and 4.0 equivalents. The reaction time will be dependent on the starting alcohol but between 60 minutes and 400 minutes.

Experimentally, the alcohol is charged and then dried under vacuum under hot conditions. After returning to atmospheric pressure and inserting with nitrogen, the acid catalyst is introduced and an oxetane derivative is gradually added to the medium over a time of between 60 and 180 min. At the end of the reaction, the content of residual oxetane derivative is monitored and, after cooling, the product can be packaged as is or neutralized by a base.

Stage b): Alkoxylation:

The acid catalyst introduced during stage a) can optionally be neutralized beforehand. This neutralization can in particular be carried out by several successive washing operations at 80° C. with an aqueous sodium hydrogencarbonate solution.

After drying under vacuum, the introduction of oxide is carried out at between 100° C. and 150° C. and preferably at 125° C. in the case of ethylene oxide, in the presence of 0.15, with respect to the final product, of potassium hydroxide, for example. The amount of oxide involved will be adjusted to the degree of alkoxylation targeted.

At the end of the addition, the reaction medium is maintained at constant temperature and at constant pressure and is finally freed from inorganic products by treating over magnesium silicate with the aim of removing all catalytic residues.

The analytical characteristics of various examples of amphiphilic structures obtained according to the preparation protocols described above are presented in the following table 1.

The curves in FIG. 1 fully show the surfactant nature of the two derivatives R and S. At a concentration equal to 1000 mg/l, the surface tensions of the water are respectively equal to 33.9 and 39.3 mN/m.

2) Wetting Properties

The wetting of a solid by a liquid corresponds to the spreading of the liquid over the solid. By reducing the surface tension, the wetting agents make possible greater spreading of the liquid.

Principle of the Measurement

Wetting power was determined on raw cotton, according to a methodology adapted from that described in standard NFT 73420, at two temperatures, 20° C. and 60° C., and at a concentration of surfactants equal to 0.6 g/l in deionized water, with or without sodium hydroxide. It is assessed by the measurement of the duration of wetting of a disk of raw cotton placed in a solution of surfactants at a defined concentration.

Experimental Protocol 700 ml of a test solution comprising 0.6 g/l of surface-active material in deionized water are prepared. The test solution is placed in a beaker thermostatically controlled at the desired temperature (20° C. and 60° C., ±1° C.)

The experimental measurement can be carried out at the neutral pH of the deionized water or in a basic medium in the presence of sodium hydroxide.

A disk of raw cotton, corresponding to the standard NFT 73-406 (30 mm in diameter), is placed at the surface of the solution prepared above using immersion tongs specific to this test.

The duration of wetting is determined experimentally using a stopwatch. The time $t_0$ corresponds to the moment

TABLE 1

Characteristics of the "trimethylolpropane oxetane (R = Et)/alcohol" reaction products, with or without ethylene oxide ($Z_1 = Z_2 = H$).

| Ref. | Alcohol of formula (II) | Stoich. mol. TMPO | Degree of ethox. (m) | Degree of ethox. (A + B) | Appearance at AT | pH 1% pH 10% | Water (%) | M. p. (° C.) Visco at 25° C. (cPs) | $N_A$ (mg KOH/g) | $N_{OH}$ (mg KOH/g) | Res. TMPO (%) | Res. alcohol(s) (%) |
|---|---|---|---|---|---|---|---|---|---|---|---|---|
| Q | C10 oxo | 2.6 eq. | 0 | 5 | Liquid | 4.4 | 0.11 | 1915 | 0.17 | 282.6 | <0.1 | 1.0 |
| R | C10 oxo | 2.6 eq. | 0 | 10 | Liquid | 5.5 | 0.14 | 866 | 0.13 | 207.0 | <0.1 | 0.3 |
| S | C10 oxo | 2.6 eq. | 0 | 20 | Liquid | 5.3 | 0.31 | 598 | 0.16 | 133.7 | <0.1 | <0.1 |
| T | Decanol | 0.5 eq. | 6 | 0 | Liquid | 3.3 | 0.24 | 68 | 3.95 | 175.9 | <0.02 | 1.7 |
| U | Decanol | 0.75 eq. | 6 | 0 | Liquid | 3.4 | 0.33 | 118 | 3.67 | 194.2 | <0.02 | 1.4 |
| V | Decanol | 1 eq. | 6 | 0 | Liquid | 3.4 | 0.27 | 174 | 3.51 | 212.1 | <0.02 | 1.1 |
| V1 | Decanol | 1.5 eq. | 6 | 0 | Liquid | 3.6 | 0.19 | 1344 | 3.13 | 243.5 | <0.02 | 0.8 |

$N_A$ means acid number,
$N_{OH}$ means hydroxyl number,
AT means ambient temperature.

Example 2

Evaluation of the Emulsifying Properties

The various tests below are intended to demonstrate the surface-active nature of the derivatives listed in table 1. For each test, the choice of the structures studied was guided by the solubility in water and the order of magnitude of the HLB of these structures.

1) Lowering of the Surface Tension of Water

The tensiometry measurements were carried out at 20° C. in deionized water using a K12™ tensiometer. Only the water soluble derivatives R and S (table 1) were tested and the curves for lowering the surface tension (expressed in mN/m) of the water are collated in FIG. 1.

when the bottom part of the disk touches the solution and the time $t_{final}$ corresponds to the moment when the disk sinks by itself into the solution. Ten consecutive measurements are carried out with the same solution, care being taken, however, to discard the cotton disks used after each measurement.

Expression of the Results

The wetting power is expressed in seconds and it corresponds to the mean of the ten measurements carried out.

Final Results Obtained

The derivates R to V (table 1) were tested and the impregnation times were compared with those corresponding to an ethoxylated and propoxylated C10 Oxo alcohol sold by SEPPIC under the name Simulsol™ NW 342 or to ethoxylated C10 Oxo alcohols (table 2).

TABLE 2

Wetting properties of the derivatives R to V

| Surfactant ref. | Time in sec. at 20° C. | Time in sec. at 60° C. |
|---|---|---|
| Simulsol ™ NW 342 | 23 | 23 |
| Simulsol ™ NW 342[a] | 30 | 50 |
| Simulsol ™ NW 342[b] | 40 | 82 |
| C-10 Oxo alcohol + 4.5 EO | 13 | 8 |
| C-10 Oxo alcohol + 6.0 EO | 27 | 8 |
| R | 55 | 26 |
| S | 324 | 61 |
| T | 36 | 18 |
| U | 34 | 24 |
| V[a] | 97 | 88 |
| V[b] | 105 | 94 |
| U | 51 | 25 |

[a] in a 1% solution of sodium hydroxide in deionized water.
[b] in a 2% solution of sodium hydroxide in deionized water.

The wetting powers of the novel structures of the present invention are highly satisfactory with the systematic distinguishing feature of improving when the temperature increases.

3) Foaming Properties

The formation of foam, a dispersion of the significant volume of gas in a small volume of liquid, requires the presence of surface-active agents which are adsorbed at the water/air interface.

Principle of the Measurement

The determination of the foaming properties by bubbling nitrogen makes it possible to evaluate the possibilities which a surfactant may have to form foam.

The foam is formed by the introduction of a predetermined volume of nitrogen into a solution of surfactants.

Experimental Protocol 50 ml of a 1 g/l solution of surfactants in deionized water are introduced into a thermostatically controlled 250 ml graduated measuring cylinder. The measurements were carried out at 20 and 60° C. and the pH during the tests is that of the solutions of surfactants at the start. A gas dispensing finger with a porosity of 3 (Ref. Corning Pyrex 853-1) is positioned in such a way that the end of the centered nozzle is found one centimeter from the bottom of the measuring cylinder. The nitrogen flow rate is then precisely adjusted to 50 l/h and sparging is carried out for 15 seconds. At the end of this period of time, the delivery of nitrogen is halted and the experimenter records the initial volume of foam and the volume of foam after thirty seconds, one minute, two minutes and thirty minutes. Three tests were carried out in different measuring cylinders for the same surfactant solution.

Results Obtained

The derivatives R to V (table 1) were tested and the foam heights recorded at different times were compared with those obtained with ethoxylated C-10 Oxo alcohols (table 3).

TABLE 3

Foaming properties of the R to V derivatives

| Surfactant reference | 20° C. | 60° C. |
|---|---|---|
| | Foam height in cm after 0/1/2/30 min | |
| C-10 Oxo alc. + 4.5 EO | 150/nd/115/10 | 155/nd/30/5 |
| C-10 Oxo alc. + 6.0 EO | 153/nd/123/25 | 160/nd/103/15 |
| R | 148/120/110/20 | 155/115/45/0 |
| S | 150/120/110/18 | 175/135/135/0 |

TABLE 3-continued

Foaming properties of the R to V derivatives

| Surfactant reference | 20° C. | 60° C. |
|---|---|---|
| | Foam height in cm after 0/0.5/1/2/30 min | |
| T | 178/nd/nd/130/25 | 180/nd/nd/130/0 |
| U | 148/nd/nd/113/13 | 168/135/83/20/0 |
| V | 140/100/65/38/10 | 125/20/13/5/0 |

The foaming powers of the novel structures described are comparable to those of the references chosen and thus testify to their surface-active nature.

4) Oil-in-Water Emulsifying Properties

The oil-in-water emulsifying power was assessed by varying the nature of the surfactant (Q, S—table 1), the nature of the oil and the proportion of each ingredient. Various emulsification protocols were employed.

Emulsion 1:
the surfactant is dispersed in the oil at 60° C.,
half the water is added over 1 min at 1000 rev/min,
the mixture is sheared for 3 min at 4000 rev/min with a shearing stirrer comprising a rotary-stator system sold by Silverson™,
the other half of the water is added over 1 min at 1000 rev/min,
the mixture is sheared for 1 min at 4000 rev/min with a shearing stirrer comprising a rotary-stator system sold by Silverson™,
the mixture is cooled to 30° C. while stirring with an anchor stirrer at 200 rev/min.

Emulsions 2 and 3:
the surfactant and the oil are homogenized at 60° C. while stirring with an anchor stirrer at 200 rev/min,
the water is added and the mixture is homogenized for 5 min,
the mixture is sheared for 3 min at 4000 rev/min with a shearing stirrer comprising a rotary-stator system sold by Silverson™,
the mixture is cooled to 30° C. while stirring with an anchor stirrer at 200 rev/min.

Emulsion 4:
the surfactant and the water are mixed at 80° C.,
the oil is added and stirring is carried out with a spatula,
the mixture is sheared for 4 min at 8000 rev/min with a shearing stirrer comprising a rotary-stator system sold by Silverson™,
the mixture is cooled to ambient temperature with gentle stirring with an anchor stirrer.

The stability of each emulsion was subsequently monitored over time at ambient temperature and at 40° C. (table 4).

TABLE 4

Stabilities of the oil-in-water emulsions

| Surfactant (emulsion reference) | Oil nature | Composition surfactant/ oil/water | t = 1 day Ambient | Observations t = variable Ambient | t = variable 40° C. |
|---|---|---|---|---|---|
| 20% of Q + 80% of Montane ™ 80[a] | Rapeseed oil | 5/50/45 | Em.[b]: 100% | Em.[b]: 100% (8 days) | Em.[b]: 100% (8 days) |

TABLE 4-continued

Stabilities of the oil-in-water emulsions

| Surfactant (emulsion reference) | Oil nature | Composition surfactant/ oil/water | Observations t = 1 day Ambient | t = variable Ambient | 40° C. |
|---|---|---|---|---|---|
| (Emulsion 1) 50% of Q + 50% of S | Exxsol D 100 | 2/20/78 | Em.[b]: 100% | Em.[b]: ~85% (7 days) | Em.[b]: ~85% (7 days) |
| (Emulsion 2) 25% of Q + 75% of S | Exxsol D 100 | 2/20/78 | Em.[b]: ~98% | Em.[b]: ~90% (7 days) | Em.[b]: ~90% (7 days) |
| (Emulsion 3) (Emulsion 4) | Triglyceride 5545 | 5/50/45 | Em.[b]: ~100% | Em.[b]: ~99% (30 days) | Em.[b]: ~50% (30 days) |

[a]Sorbitan monoleate, sold by Seppic
[b]Em: Proportion of liquid occurring in a homogeneous emulsion form, evaluated using a graduation on the storage container used in the stability study.

The results demonstrate advantageous oil-in-water emulsifying powers when the surfactants tested are combined with one another or with other surfactants (Montane™ 80 results in unstable oil-in-water emulsions).

5) Water-in-Oil Emulsifying Properties

Similarly, the water-in-oil emulsifying power was assessed by varying the nature of the surfactant, the nature of the oil and the proportion of each ingredient. The emulsification protocol employed is as follows:
- the surfactant and the oil are mixed at 80° C.,
- water additivated with $MgSO_4$ is added,
- the mixture is sheared for 4 min at 8000 rev/min with a shearing stirrer comprising a rotary-stator system by Silverson™,
- the mixture is cooled to ambient temperature with gentle stirring using an anchor stirrer.

The stability of each emulsion was subsequently monitored over time at ambient temperature and at 40° C.

The results bring to the fore emulsifying powers far superior to those of Montane™ 60 (sorbitan monostearate, sold by Seppic), taken as reference.

Example 3

Formulations

In the following formulae, the percentages are expressed by weight of the formulation:

3.1 Foaming Gel for the Face
Formula

| A | Sodium lauryl sulfate | 5.9% |
|---|---|---|
|   | Water | q.s. for 100% |
| B | Compound V according to the invention | 5.0% |
|   | Montaline ™ C40 | 5.0% |
|   | Sepitonic ™ M3 | 1.0% |
|   | Fragrance | 0.1% |
|   | Kathon ™ CG | 0.08% |
| C | Lactic acid | 0.15% |
|   | Sodium chloride | 0.8% |
| D | Colorant | 0.05% |
| E | Sodium chloride | q.s. |

Procedure

Phase A is prepared in a fume cupboard. The ingredients of phase B are mixed while homogenizing after each addition. A is subsequently poured into B. C is added, followed by D. The viscosity is adjusted, if necessary, by adding E (1.5% max.).

3.2 Foaming Bath for Children
Formula

| A | Oronal ™ LCG | 10.00% |
|---|---|---|
|   | Compound V according to the invention | 13.00% |
|   | Fragrance | 00.10% |
|   | Sepicide ™ HB | 00.50% |
| B | Water | 20.00% |
|   | Capigel ™ 98 | 04.50% |
| C | Water | q.s. for 100% |
|   | Sepicide ™ CI | 00.30% |
|   | Colorant | q.s. |
|   | Sodium hydroxide | q.s. |

Procedure

Oronal™ LOG is mixed with the surfactant according to the invention, the fragrance and the preservative. The Capigel™ is diluted in a portion of the water and added to the surfactants, and then the remaining water is added. The Sepicide™ CI and the colorant are added and then the pH is adjusted to approximately 7.2.

3.3 Liquid Soap for the Hands
Formula

| A | Compound T according to the invention | 10.00% |
|---|---|---|
|   | Amonyl ™ 675SB | 10.00% |
|   | Fragrance | 00.30% |
|   | Sepicide ™ HB | 00.50% |
| B | Water | q.s. for 100% |
|   | Sepicide ™ CI | 00.30% |
|   | Sodium chloride | q.s. |

Procedure

The ingredients of phase A are mixed and then phase B is added.

3.4 Cleansing Foam for the Face
Formula

| A | Proteol ™ Oat | 3.00% |
|---|---|---|
|   | Compound W according to the invention | 10.00% |
|   | Sepicide HB ™ | 00.50% |
|   | Fragrance | 00.20% |
| B | Water | q.s. for 100% |
|   | Sepicide ™ CI | 00.30% |
|   | Sepitonic M3 | 01.00% |
|   | Tromethamine | q.s. |
|   | Colorant | q.s. |

Procedure

The fragrance and the preservative are dissolved in the mixture of the surfactants (A). The water is added, followed by the other ingredients in succession.

3.5 Cleansing Wipes
Formula

| A | Compound V according to the invention | 02.00% |
|---|---|---|
|   | Aquaxyl ™ | 01.00% |
| B | Sepicide ™ $HB_2$ | 00.50% |
|   | Fragrance | 00.05% |
|   | Hexylene glycol | 10.00% |
| C | Water | q.s. for 100% |

Procedure

The ingredients of phase B are mixed until clarity is achieved and then this phase is added to phase A. C is added.

3.6 Antibacterial Liquid Salt

| | |
|---|---|
| Compound V according to the invention | 15.00% |
| Chlorhexidine digluconate | 00.20% |
| Oramide ™ DL 200 AF | 03.00% |
| Water | q.s. for 100 |
| Fragrance | 00.05% |
| Colorant | q.s. |
| Sodium chloride | q.s. |

Procedure

The constituents are added and mixed in the order shown.

3.7 Conditioning Shampoo

| | | |
|---|---|---|
| A | Cetyltrimethylammonium chloride | 03.50% |
| | Compound V according to the invention | 25.00% |
| | Dimethicone copolyol | 01.00% |
| | Fragrance | 00.50% |
| | Amonyl ™ 380BA | 11.00% |
| | Kathon ™ CG | 0.08% |
| B | Polyquaternium ™ 10 | 00.30% |
| | Lactic acid | q.s. |
| | Water | q.s. for 100% |
| | Colorant | q.s. |
| | Lactic acid | q.s. pH = 6 |

Procedure

Phase B is prepared separately: mixing is carried out until clarity is achieved. The ingredients are carefully mixed in the order shown.

3.8 Care Cream

| | |
|---|---|
| Cyclomethicone | 10% |
| Simulgel EG | 3.0% |
| Compound K according to the invention | 2% |
| Stearyl alcohol | 1% |
| Stearic alcohol | 0.5% |
| Preservative | 0.65% |
| Lysine | 0.025% |
| EDTA (disodium salt) | 0.05% |
| Xanthan gum | 0.2% |
| Glycerol | 3% |
| Water | q.s. for 100% |

3.9 AntiSun Milk

Formula

| | | |
|---|---|---|
| A | Compound E according to the invention | 3.0% |
| | Sesame oil | 5.0% |
| | Parsol ™ MCX | 5.0% |
| | λ-Carrageenan | 0.10% |
| B | Water | q.s. for 100% |
| C | Simulgel EG | 3.00% |
| D | Fragrance | q.s. |
| | Preservative | q.s. |

Procedure

B is emulsified in A at 75° C., then C is added at approximately 60° C., then D is added at approximately 30° C. and the pH is adjusted, if necessary.

3.10 Moisturizing and Mattifying Foundation

Formula

| | | |
|---|---|---|
| A | Water | 20.0% |
| | Butylene glycol | 4.0% |
| | PEG-400 | 4.0% |
| | Pecosil ™ PS100 | 1.0% |
| | Sodium hydroxide | q.s. pH = 9 |
| | Titanium dioxide | 7.0% |
| | Talc | 2.0% |
| | Yellow Iron oxide | 0.8% |
| | Red iron oxide | 0.3% |
| | Black iron oxide | 0.05% |
| B | Lanol ™ 99 | 8% |
| | Caprylic/capric triglyceride | 8% |
| | Compound G according to the invention | 5.00% |
| C | Water | q.s. for 100% |
| | Micropearl ™ M305 | 2.0% |
| | Tetrasodium EDTA | 0.05% |
| D | Cyclomethicone | 4.0% |
| | Xanthan gum | 0.2% |
| | Simulgel NS | 3.0% |
| E | Sepicide ™ HB | 0.5% |
| | Sepicide CI | 03% |
| | Fragrance | 0.2% |

Procedure

The mixtures B+D and A+C are prepared at 80° C., then mixing is carried out and the combination is emulsified.

3.11 Body Milk

| | |
|---|---|
| Compound E according to the invention | 3.5% |
| Lanol ™ 37T | 8.0% |
| Solagum ™ L | 0.05% |
| Water | q.s. for 100% |
| Benzophenone-3 | 2.0% |
| Dimethicone 350 cPs | 0.05% |
| Simulgel EG | 3.0% |
| Preservative | 0.2% |
| Fragrance | 0.4% |

3.12 Makeup-Removing Emulsion Comprising Sweet Almond Oil

| | |
|---|---|
| Compound L according to the invention | 5% |
| Sweet almond oil | 5% |
| Water | q.s. for 100% |
| Simulgel EG | 2.5% |
| Glycerol | 5% |
| Preservative | 0.2% |
| Fragrance | 0.3% |

3.13 Moisturizing Cream for Greasy Skin

| | |
|---|---|
| Compound L according to the invention | 5% |
| Cetylstearyl octanoate | 8% |
| Octyl palmitate | 2% |
| Water | q.s. for 100% |
| Simulgel NS | 2.5% |
| Micropearl ™ M100 | 3.0% |
| Mucopolysaccharides | 5% |
| Sepicide ™ HB | 0.8% |
| Fragrance | 0.3% |

3.14 Cream Comprising AHAs for Sensitive Skin

| | |
|---|---|
| Mixture of N-laurylamino acids | 0.1% to 5% |
| Magnesium potassium aspartate | 0.002% to 0.5% |
| Lanol ™ 99 | 2% |
| Compound L according to the invention | 5.0% |
| Water | q.s. for 100% |
| Simulgel EG | 3.0% |
| Gluconic acid | 1.50% |
| Triethanolamine (TEA) | 0.9% |
| Sepicide ™ HB | 0.3% |
| Sepicide ™ CI | 0.2% |
| Fragrance | 0.4% |

3.15 Makeup-Removing Milk

| | |
|---|---|
| Compound E according to the invention | 3% |
| Primol ™ 352 | 8.0% |
| Sweet almond oil | 2% |
| Water | q.s. for 100% |
| Simulgel NS | 3.0% |
| Preservative | 0.2% |

3.16 AntiSun Milk

| | |
|---|---|
| Compound E according to the invention | 3.5% |
| Lanol ™ 37T | 10.0% |
| Parsol ™ MCX | 5.0% |
| Eusolex ™ 4360 | 2.0% |
| Water | q.s. for 100% |
| Simulgel 600 | 3.0% |
| Preservative | 0.2% |
| Fragrance | 0.4% |

3.17 Cream Comprising AHAs

| | |
|---|---|
| Compound L according to the invention | 5.0% |
| Deepaline ™ PVB | 1.05% |
| Lanol ™ 99 | 10.0% |
| Water | q.s. for 100% |
| Gluconic acid | 1.5% |
| TEA (triethanolamine) | 0.9% |
| Simulgel EG | 3.0% |
| Fragrance | 0.4% |
| Sepicide ™ HB | 0.2% |
| Sepicide ™ CI | 0.4% |

3.18 Sunless Tanning Emulsion

| | |
|---|---|
| Lanol ™ 99 | 15% |
| Compound L according to the invention | 5.0% |
| Parsol ™ MCX | 3.0% |
| Water | q.s. for 100% |
| Dihydroxyacetone | 5.0% |
| Monosodium phosphate | 0.2% |
| Simulgel EG | 2.5% |
| Fragrance | 0.3% |
| Sepicide ™ HB | 0.8% |
| Sodium hydroxide | q.s. pH = 5 |

3.19 Care Cream

| | |
|---|---|
| Cyclomethicone | 10% |
| Simulgel NS | 3.0% |
| Compound L according to the invention | 4.5% |
| Preservative | 0.65% |
| Lysine | 0.025% |
| EDTA (disodium salt) | 0.05% |
| Xanthan gum | 0.2% |
| Glycerol | 3% |
| Water | q.s. for 100% |

3.20 Body Milk Formula

| | | |
|---|---|---|
| A | Compound E according to the invention | 3.0% |
| | Glycerol triheptanoate | 10.0% |
| B | Water | q.s. for 100% |
| C | Simulgel NS | 3.0% |
| D | Fragrance | q.s. |
| | Preservative | q.s. |

Procedure

A is melted at approximately 75° C. B is emulsified in A at 75° C., then C is added at approximately 60° C. and then D is added.

3.21 Cream Comprising AHAs

| | |
|---|---|
| Compound K according to the invention | 5.0% |
| Deepaline ™ PVB | 1.05% |
| Lanol ™ 99 | 10.0% |
| Water | q.s. for 100% |
| Gluconic acid | 1.5% |
| TEA (triethanolamine) | 0.9% |
| Simulgel 600 | 1.5% |
| Fragrance | 0.4% |
| Sepicide ™ HB | 0.2% |
| Sepicide ™ CI | 0.4% |

3.22 Makeup-Removing Milk

| | |
|---|---|
| Simulsol ™ 165 | 4% |
| Compound G according to the invention | 1% |
| Caprylic/capric triglyceride | 15% |
| Pecosil ™ DCT | 1% |
| Demineralized water | q.s. |
| Capigel ™ 98 | 0.5% |
| Simulgel EG | 3% |
| Proteol ™ APL | 2% |
| Sodium hydroxide | q.s. for pH = 7 |

3.23 AntiSun Cream

| | |
|---|---|
| Simulsol ™ 165 | 3% |
| Compound G according to the invention | 2% |
| $C_{12}$-$C_{15}$ benzoate | 8% |
| Pecosil ™ PS 100 | 2% |
| Dimethicone | 2% |
| Cyclomethicone | 5% |
| Octyl para-methoxycinnamate | 6% |
| Benzophenone-3 | 4% |
| Titanium oxide | 8% |
| Xanthan gum | 0.2% |
| Butylene glycol | 5% |

-continued

| Demineralized water | q.s. for 100% |
|---|---|
| Simulgel NS | 2.5% |
| Preservative, fragrance | q.s. |

3.2 Vitamin Cream

| Simulsol ™ 165 | 5% |
|---|---|
| Compound G according to the invention | 1% |
| Caprylic/capric triglycerides | 20% |
| Vitamin A palmitate | 0.2% |
| Vitamin E acetate | 1% |
| Micropearl ™ M 305 | 1.5% |
| Simulgel EG | 3% |
| Water | q.s. for 100% |
| Preservative, fragrance | q.s. |

3.25 Antisun and Self-Tanning Gel

| Compound E according to the invention | 3.0% |
|---|---|
| Glyceryl triheptanoate | 10.0% |
| Deepaline ™ PVB | 1.05% |
| Simulgel 600 | 2.2% |
| Water | q.s. for 100% |
| Dihydroxyacetone | 5% |
| Fragrance | 0.1% |
| Sepicide ™ HB | 0.3% |
| Sepicide ™ CI | 0.1% |
| Parsol ™ MCX | 4.0% |

3.26 Self-Tanning Cream Comprising α-Hydroxy Acids

| Compound G according to the invention | 5.0% |
|---|---|
| Deepaline ™ PVB | 1.05% |
| Lanol ™ 99 | 10.0% |
| Water | q.s. 100% |
| Gluconic acid | 1.5% |
| Dihdyroxyacetone | 3% |
| Triethanolamine | 0.9% |
| Simulgel NS | 3.0% |
| Fragrance | 0.4% |
| Sepicide ™ HB | 0.2% |
| Sepicide ™ CI | 0.4% |

3.27 Self-Tanning Cream Comprising α-Hydroxy Acids for Sensitive Skin

| Mixture of N-lauroylamino acids | 0.1% to 5% |
|---|---|
| Magnesium potassium aspartate | 0.002% to 0.5% |
| Compound H according to the invention | 5.0% |
| Lanol ™ 99 | 2.0% |
| Water | q.s. 100% |
| Lactic acid | 1.5% |
| Dihydroxyacetone | 3.5% |
| Triethanolamine | 0.9% |
| Simulgel NS | 1.5% |
| Fragrance | 0.4% |
| Sepicide ™ HB | 0.3% |
| Sepicide ™ CI | 0.2% |

3.28 Industrial Degreaser

| Compound U according to the invention | 5% |
|---|---|
| Sodium bicarbonate | 3.5% |
| Sodium hydrogencarbonate | 3.5% |
| EDTA, disodium salt | 5% |
| Polymer AC | 0.2% |
| Seppic 1050 | 1.5% |
| Triton H 66 | 3.5% |
| Simulsol PG 711 | 2.0% |
| Water | q.s. 100% |

Sepitonic™ M3, a mixture of magnesium aspartate, zinc gluconate and copper gluconate, is an energizing active principle sold by Seppic.

Polyquaternium™ 10 is a quaternary ammonium salt of a hydroxyethylcellulose, sold by Amerchol under the name Ucare Polymer JR-400.

Kathon™ CG, a mixture of methylchloroisothiazolinone and methylisothiazolinone, is a preservative sold by Röhm & Haas.

Oronal™ LCG, a mixture of PEG-40 glyceryl cocoate and sodium coceth sulfate, is a foaming agent sold by Seppic.

Amonyl™ 675SB is a cocamidopropyl hydroxy sultaine, sold by Seppic.

Sepicide™ HB, a mixture of phenoxyethanol, methylparaben, ethylparaben, propylparaben and butylparaben, is a preservative sold by Seppic.

Capigel™ 98 is a copolymer of acrylates, sold by Seppic.

Sepicide™ CI, imidazoline urea, is a preservative sold by Seppic.

Sepicide™ HB2, a mixture of phenoxyethanol, methylparaben, ethylparaben, propylparaben, butylparaben and isobutylparaben, is a preservative sold by Seppic.

Preteol™ Oat is a mixture of N-laurylamino acids obtained by complete hydrolysis of oat protein, as described in WO 94/26694, sold by Seppic.

Montaline™ C40 is a cocamidopropyl betainamide monoethanolamine chloride salt.

Aquaxyl™ is a moisturizing active principle comprising a mixture of xylitolpolyglucosides, anhydroxylitol and xylitol, sold by Seppic.

Oramide™ DL 200 AF is a cocamide diethanolamine, sold by Seppic.

Amonyl™ 380BA is a cocamidopropyl betaine, sold by Seppic.

Lanol™ 99 is isononyl isononanoate, sold by Seppic.

Micropearl™ 100 is an ultrafine powder which is very soft to the touch and which has a mattifying action, sold by Matsumo.

Micropearl™ M 305 is an ultrafine powder which is very soft to the touch and which has a mattifying action, sold by Matsumo.

Sepicide™ CI, imidazoline urea, is a preservative sold by Seppic.

Pemulen™ TR1 is an acrylic polymer, sold by Goodrich.

Simulsol™ 165 is self-emulsifying glycerol stearate, sold by Seppic.

Parsol™ MCX is octyl para-methoxycinnamate, sold by Givaudan.

Lanol™ 37T is glycerol triheptanoate, sold by Seppic.

Solagum™ L is a carrageenan, sold by Seppic.

Eusolex™ 4360 is a sunscreen sold by Merck.

Deepaline™ PVB is an acylated wheat protein hydrolysate, sold by Seppic.

Proeteol™ APL is a foaming surfactant sold by Seppic.

Primol™ 352 is a mineral oil, sold by Exxon.

Pecosil™ DCT is Sodium Dimethicone PEG-7 Acetyl Methyltaurate, sold by Phoenix.

Pecosil™ PS100 is Dimethicone PEG-7 Phosphate, sold by Phoenix.

Simulgel™ EG is a self-invertible inverse latex of copolymers, such as those described in international publication WO 99/36495 (INCI name: Sodium Acrylate/Sodium Acryloyldimethyl Taurate Copolymer and Isohexadecane and Polysorbate 80), sold by Seppic.

Simulgel™ NS is a self-invertible inverse latex of copolymers, such as those described in international publication WO 99/36445 (INCI name: Hydroxyethyl Acrylate/Sodium Acryloyldimethyl Taurate Copolymer and Squalane and Polysorbate 60), sold by Seppic.

Simulgel™ 600 is a self-invertible inverse latex (INCI name: Acrylamide/Sodium Acryloldimethyl Taurate Copolymer/Isohexadecane/Polysorbate 80) sold by Seppic.

Polymer AC is a poly(sodium acrylate) used as dispersing agent.

Triton H 66 is ethoxylated m,p-cresol phosphate, used as hydrophobic agent and solubilizing agent.

Simulsol PG 711 is a propoxylated derivative of stearyl alcohol used as antifoaming agent.

Seppic 1050 is a composition comprising monoethanolamine citrate and monoethanolamine tartrate used as corrosion-inhibitor.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A compound of formula (I):

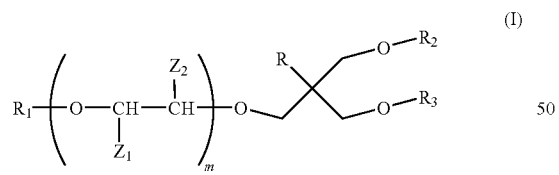

in which:
R$_1$ represents a linear or branched and saturated or unsaturated aliphatic radical comprising from 3 to 24 carbon atoms, optionally substituted by one or more hydroxyl groups, R represents a linear or branched alkyl radical comprising from 1 to 8 carbon atoms, optionally substituted by a hydroxyl radical, m represents a number greater than or equal to 0 and less than or equal to 150, Z$_1$ and Z$_2$, which are identical or different, are selected from H, CH$_3$ or CH$_2$—CH$_3$, R$_2$ represents either a hydrogen atom or a monovalent radical of formula (a) and R$_3$ represents a monovalent radical of formula (a):

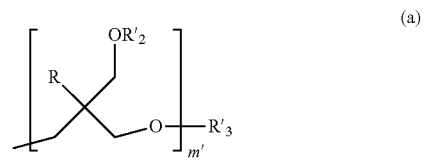

in which:
m' represents a number from 1 to 10,

R'$_2$ represents either a hydrogen atom or a monovalent radical of formula (b):

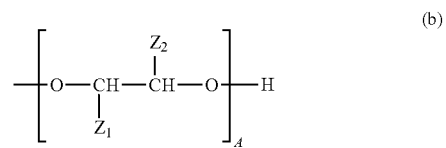

in which:
Z$_1$ and Z$_2$, which are identical or different, are selected from H, CH$_3$ or CH$_2$—CH$_3$, A represents an integer greater than or equal to 0 and less than or equal to 50, R'$_3$, which is identical to R'$_2$ or different from R'$_2$, represents either a hydrogen atom or a monovalent radical of formula (c):

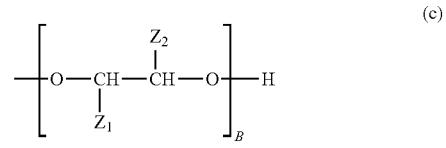

in which:
Z$_1$ and Z$_2$, which are identical or different, are selected from H, CH$_3$ or CH$_2$—CH$_3$, B represents an integer greater than or equal to 0 and less than or equal to 50, with A+B greater than or equal to 0 and less than or equal to 50 and m+A+B≠0.

2. The compound of claim 1, where the formula (a) is:

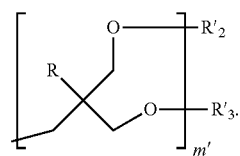

3. A compound of formula ($I_0$) that corresponds to the formula (I) of claim 1 in which $R_2$ represents a hydrogen atom and $R_3$ represents a radical of formula (a'):

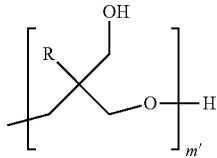

(a')

that corresponds to the formula (a) of claim 1 in which $R'_2$ and $R'_3$ each represent a hydrogen atom.

4. A compound of formula ($I'_0$) that corresponds to the formula (I) of claim 1 in which $R_2$ and $R_3$ represent a radical of formula (a'):

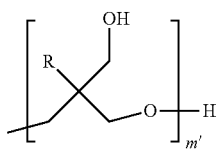

(a')

that corresponds to the formula (a) of claim 1 in which $R'_2$ and $R'_3$ each represent a hydrogen atom.

5. A compound of formula ($I_1$) that corresponds to the formula (I) of claim 1 in which $R'_2$ and $R'_3$ represent a hydrogen atom.

6. A compound of formula ($I_2$) that corresponds to formula (I) of claim 1 in which one or other among $R'_2$ and $R'_3$ does not represent a hydrogen atom.

7. The compound of formula (I) of claim 1, wherein A and B are identical.

8. The compound of formula (I) of claim 1, in which R is selected from the methyl, ethyl, propyl, butyl, pentyl, hexyl, heptyl, octyl or methylol radicals.

9. A composition comprising at least one compound of formula (II):

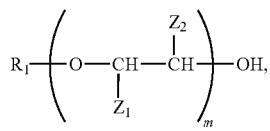

(II)

in which $R_1$ represents a linear or branched and saturated or unsaturated aliphatic radical comprising from 3 to 24 carbon atoms, optionally substituted by one or more hydroxyl groups, $Z_1$ and $Z_2$, which are identical or different, are selected from H, $CH_3$ or $CH_2$—$CH_3$, and a mixture of at least one compound selected from the compounds of formula (I)

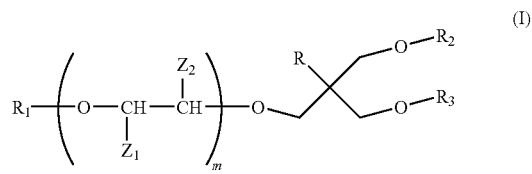

(I)

in which:

$R_1$ represents a linear or branched and saturated or unsaturated aliphatic radical comprising from 3 to 24 carbon atoms, optionally substituted by one or more hydroxyl groups, R represents a linear or branched alkyl radical comprising from 1 to 8 carbon atoms, optionally substituted by a hydroxyl radical, m represents a number greater than or equal to 0 and less than or equal to 150, $Z_1$ and $Z_2$, which are identical or different, are selected from H, $CH_3$ or $CH_2$—$CH_3$, $R_2$ and $R_3$, which are identical or different, represent either a hydrogen atom or a monovalent radical of formula (a):

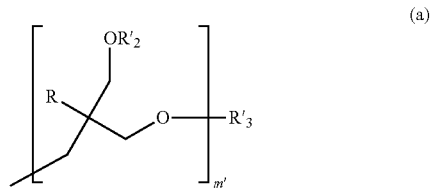

(a)

in which:

m' represents a number from 1 to 10, $R'_2$ represents either a hydrogen atom or a monovalent radical of formula (b):

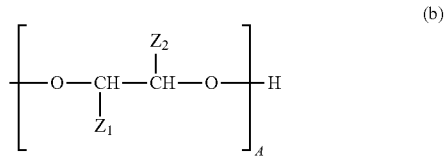

(b)

in which:

$Z_1$ and $Z_2$, which are identical or different, are selected from H, $CH_3$ or $CH_2$—$CH_3$, A represents an integer greater than or equal to 0 and less than or equal to 50, $R'_3$, which is identical to $R'_2$ or different from $R'_2$, represents either a hydrogen atom or a monovalent radical of formula (c):

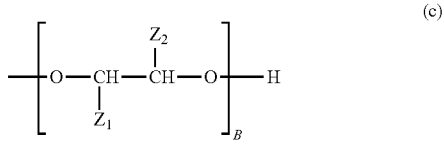

in which:

Z₁ and Z₂, which are identical or different, are selected from H, CH₃ or CH₂—CH₃, B represents an integer greater than or equal to 0 and less than or equal to 50, with A+B greater than or equal to 0 and less than or equal to 50 and m+A+B≠0, wherein formula ($I_1$) that corresponds to the formula (I) in which $R'_2$ and $R'_3$ represent a hydrogen atom or ($I_2$) that corresponds to formula (I) in which one or other among $R'_2$ and $R'_3$ does not represent a hydrogen atom.

10. A process for the preparation of a compound of formula ($I_1$) that corresponds to the formula (I)

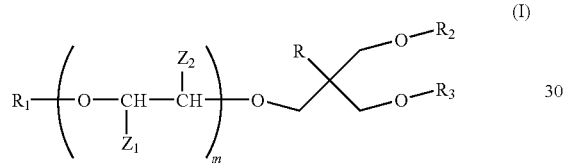

in which:

$R_1$ represents a linear or branched and saturated or unsaturated aliphatic radical comprising from 3 to 24 carbon atoms, optionally substituted by one or more hydroxyl groups, R represents a linear or branched alkyl radical comprising from 1 to 8 carbon atoms, optionally substituted by a hydroxyl radical, m represents a number greater than or equal to 0 and less than or equal to 150, Z₁ and Z₂, which are identical or different, are selected from H, CH₃ or CH₂—CH₃, R₂ and R₃, which are identical or different, represent either a hydrogen atom or a monovalent radical of formula (a):

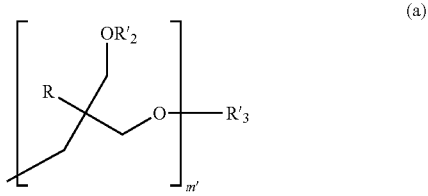

in which:

m' represents a number from 1 to 10, $R'_2$ represents either a hydrogen atom or a monovalent radical of formula (b):

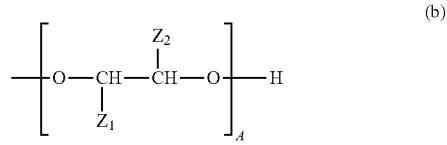

in which:

Z₁ and Z₂, which are identical or different, are selected from H, CH₃ or CH₂—CH₃, A represents an integer greater than or equal to 0 and less than or equal to 50, $R'_3$, which is identical to $R'_2$ or different from $R'_2$, represents either a hydrogen atom or a monovalent radical of formula (c):

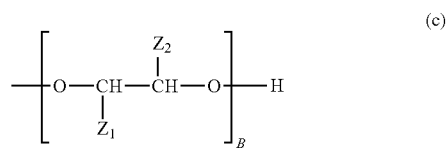

in which:

Z₁ and Z₂, which are identical or different, are selected from H, CH₃ or CH₂—CH₃, B represents an integer greater than or equal to 0 and less than or equal to 50, with A+B greater than or equal to 0 and less than or equal to 50 and m+A+B≠0, in which $R'_2$ and $R'_3$ represent a hydrogen atom, comprising the stage:

a) reaction of at least one alcohol of formula (II):

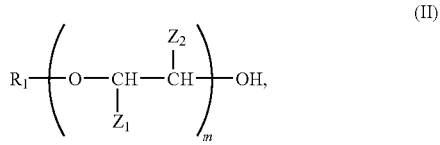

in which $R_1$ represents a linear or branched and saturated or unsaturated aliphatic radical comprising from 3 to 24 carbon atoms, optionally substituted by one or more hydroxyl groups, Z₁ and Z₂, which are identical or different, are selected from H, CH₃ or CH₂—CH₃; and at least one substrate, comprising an oxetane unit and at least one hydroxyl functional group, of formula (III):

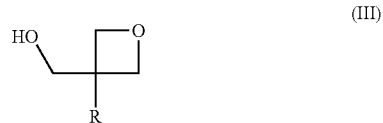

in which R represents a linear or branched alkyl radical comprising from 1 to 8 carbon atoms, optionally substituted by a hydroxyl radical; and, if necessary, the stage:

b) alkoxylation reaction of the compound of formula ($I_1$), accompanied by a catalyst 2 and by an oxide, for the preparation of a compound of formula ($I_2$) that corresponds to formula (I) in which one or other among $R'_2$ and $R'_3$ does not represent a hydrogen atom.

11. The process as defined in claim 10, wherein said at least one substrate of formula (III) is chosen from trimethylolethane-oxetane, trimethylolpropane-oxetane, trimethylolbutane-oxetane, trimethylolpentane-oxetane, trimethylolhexane-oxetane, trimethylolheptane-oxetane, trimethyloloctane-oxetane, trimethylolnonane-oxetane or pentaerythritol-oxetane.

12. A method comprising using at least one compound of the formula (I) as a nonionic surface-active agent:

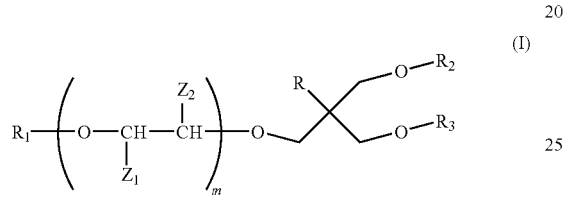

(I)

in which:
R$_1$ represents a linear or branched and saturated or unsaturated aliphatic radical comprising from 3 to 24 carbon atoms, optionally substituted by one or more hydroxyl groups,
R represents a linear or branched alkyl radical comprising from 1 to 8 carbon atoms, optionally substituted by a hydroxyl radical,
m represents a number greater than or equal to 0 and less than or equal to 150,
$Z_1$ and $Z_2$, which are identical or different, are chosen from H, $CH_3$ or $CH_2$—$CH_3$,
$R_2$ represents either a hydrogen atom or a monovalent radical of formula (a) and $R_3$ represents a monovalent radical of formula (a):

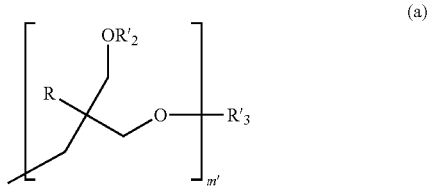

(a)

in which:
m' represents a number from 1 to 10,
$R'_2$ represents either a hydrogen atom or a monovalent radical of formula (b):

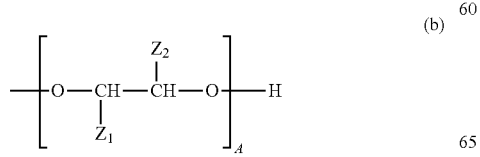

(b)

in which:
$Z_1$ and $Z_2$, which are identical or different, are chosen from H, $CH_3$ or $CH_2$—$CH_3$,
A represents an integer greater than or equal to 0 and less than or equal to 50,
$R'_3$, which is identical to $R'_2$ or different from $R'_2$, represents either a hydrogen atom or a monovalent radical of formula (c):

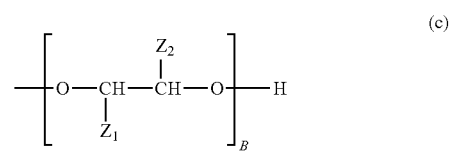

(c)

in which:
$Z_1$ and $Z_2$, which are identical or different, are chosen from H, $CH_3$ or $CH_2$—$CH_3$,
B represents an integer greater than or equal to 0 and less than or equal to 50,
with A+B greater than or equal to 0 and less than or equal to 50 and m+A+B≠0,
and/or of the composition comprising at least one compound of formula (II):

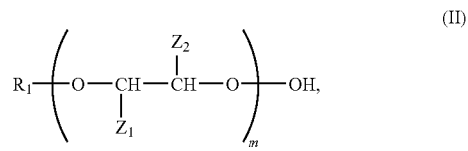

(II)

in which $R_1$ represents a linear or branched and saturated or unsaturated aliphatic radical comprising from 3 to 24 carbon atoms, optionally substituted by one or more hydroxyl groups,
$Z_1$ and $Z_2$, which are identical or different, are chosen from H, $CH_3$ or $CH_2$—$CH_3$, and
a mixture of at least one compound chosen from the compounds of formula (I) as defined hereinbefore, formula ($I_1$) in which $R'_2$ and $R'_3$ of formula (I) each represent a hydrogen atom or formula ($I_2$) in which one or other among $R'_2$ and $R'_3$ of formula (I) does not represent a hydrogen atom,
as a surface active agent.

13. The method of claim 12, wherein the at least one compound of the formula (I) is used as a foaming agent, an emulsifying agent, a wetting agent, a dispersing agent or a detergent agent.

14. A cosmetic or pharmaceutical formulation, wherein the cosmetic or pharmaceutical formulation comprises, as surface-active agent at least one compound of formula (I):

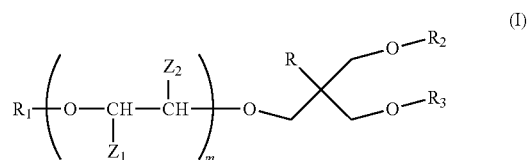

(I)

in which:

R$_1$ represents a linear or branched and saturated or unsaturated aliphatic radical comprising from 3 to 24 carbon atoms, optionally substituted by one or more hydroxyl groups, R represents a linear or branched alkyl radical comprising from 1 to 8 carbon atoms, optionally substituted by a hydroxyl radical, m represents a number greater than or equal to 0 and less than or equal to 150, Z$_1$ and Z$_2$, which are identical or different, are chosen from H, CH$_3$ or CH$_2$—CH$_3$, R$_2$ represents either a hydrogen atom or a monovalent radical of formula (a) and R$_3$ represents a monovalent radical of formula (a):

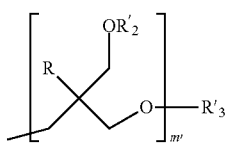
(a)

in which:

m' represents a number from 1 to 10,

R'$_2$ represents either a hydrogen atom or a monovalent radical of formula (b):

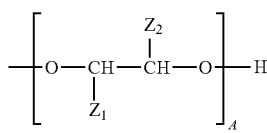
(b)

in which:

Z$_1$ and Z$_2$, which are identical or different, are chosen from H, CH$_3$ or CH$_2$—CH$_3$, A represents an integer greater than or equal to 0 and less than or equal to 50, R'$_3$, which is identical to R'$_2$ or different from R'$_2$, represents either a hydrogen atom or a monovalent radical of formula (c):

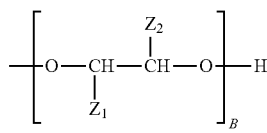
(c)

in which:

Z$_1$ and Z$_2$, which are identical or different, are chosen from H, CH$_3$ or CH$_2$—CH$_3$, B represents an integer greater than or equal to 0 and less than or equal to 50, with A+B greater than or equal to 0 and less than or equal to 50 and m+A+B≠0, and/or of the composition comprising at least one compound of formula (II):

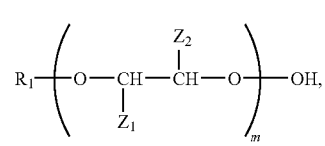
(II)

in which R$_1$ represents a linear or branched and saturated or unsaturated aliphatic radical comprising from 3 to 24 carbon atoms, optionally substituted by one or more hydroxyl groups, Z$_1$ and Z$_2$, which are identical or different, are chosen from H, CH$_3$ or CH$_2$—CH$_3$, and a mixture of at least one compound chosen from the compounds of formula (I) as defined hereinbefore, formula (I$_1$) in which R'$_2$ and R'$_3$ of formula (I) each represent a hydrogen atom or formula (I$_2$) in which one or other among R'$_2$ and R'$_3$ of formula (I) does not represent a hydrogen atom.

15. A detergent or degreasing formulation, wherein the detergent or degreasing formulation comprises, as surface-active agent, at least one compound of formula (I):

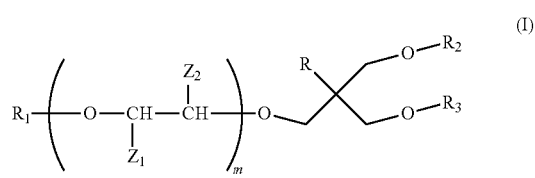
(I)

in which:

R$_1$ represents a linear or branched and saturated or unsaturated aliphatic radical comprising from 3 to 24 carbon atoms, optionally substituted by one or more hydroxyl groups, R represents a linear or branched alkyl radical comprising from 1 to 8 carbon atoms, optionally substituted by a hydroxyl radical, m represents a number greater than or equal to 0 and less than or equal to 150, Z$_1$ and Z$_2$, which are identical or different, are chosen from H, CH$_3$ or CH$_2$—CH$_3$, R$_2$ represents either a hydrogen atom or a monovalent radical of formula (a) and R$_3$ represents a monovalent radical of formula (a):

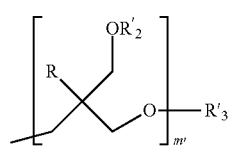
(a)

in which:

m' represents a number from 1 to 10,

R'$_2$ represents either a hydrogen atom or a monovalent radical of formula (b):

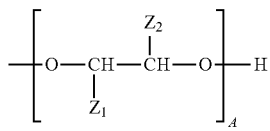
(b)

in which:

Z$_1$ and Z$_2$, which are identical or different, are chosen from H, CH$_3$ or CH$_2$—CH$_3$, A represents an integer greater than or equal to 0 and less than or equal to 50, R'$_3$, which is identical to R'$_2$ or different from R'$_2$, represents either a hydrogen atom or a monovalent radical of formula (c):

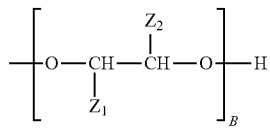
(c)

in which:

Z$_1$ and Z$_2$, which are identical or different, are chosen from H, CH$_3$ or CH$_2$—CH$_3$, B represents an integer greater than or equal to 0 and less than or equal to 50, with A+B greater than or equal to 0 and less than or equal to 50 and m+A+B≠0, and/or of the composition comprising at least one compound of formula (II):

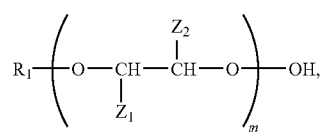
(II)

in which R$_1$ represents a linear or branched and saturated or unsaturated aliphatic radical comprising from 3 to 24 carbon atoms, optionally substituted by one or more hydroxyl groups, Z$_1$ and Z$_2$, which are identical or different, are chosen from H, CH$_3$ or CH$_2$—CH$_3$, and a mixture of at least one compound chosen from the compounds of formula (I) as defined hereinbefore, formula (I$_1$) in which R'$_2$ and R'$_3$ of formula (I) each represent a hydrogen atom or formula (I$_2$) in which one or other among R'$_2$ and R'$_3$ of formula (I) does not represent a hydrogen atom.

\* \* \* \* \*